(12) United States Patent
Lümkemann et al.

(10) Patent No.: US 11,357,914 B2
(45) Date of Patent: Jun. 14, 2022

(54) MULTI CHAMBER SYRINGE UNIT

(71) Applicant: HOFFMANN-LA ROCHE INC., Little Falls, NJ (US)

(72) Inventors: Jörg Lümkemann, Lörrach (DE); Tobias Werk, Riehen (CH)

(73) Assignee: HOFFMANN-LA ROCHE INC., Little Falls, NJ (US)

(*) Notice: Subject to any disclaimer, the term of this patent is extended or adjusted under 35 U.S.C. 154(b) by 116 days.

(21) Appl. No.: 16/075,536

(22) PCT Filed: Feb. 3, 2017

(86) PCT No.: PCT/EP2017/052432
§ 371 (c)(1),
(2) Date: Aug. 3, 2018

(87) PCT Pub. No.: WO2017/134248
PCT Pub. Date: Aug. 10, 2017

(65) Prior Publication Data
US 2019/0038836 A1  Feb. 7, 2019

(30) Foreign Application Priority Data
Feb. 5, 2016 (EP) .................................. 16154550

(51) Int. Cl.
*A61M 5/19* (2006.01)
*A61M 5/178* (2006.01)
(Continued)

(52) U.S. Cl.
CPC .............. *A61M 5/19* (2013.01); *A61J 1/2093* (2013.01); *A61M 5/284* (2013.01); *A61M 2005/1787* (2013.01); *A61M 2005/3132* (2013.01)

(58) Field of Classification Search
CPC ................ A61M 5/284; A61M 5/3129; A61M 2005/3132; A61M 2005/1787; A61J 1/2093
See application file for complete search history.

(56) References Cited

U.S. PATENT DOCUMENTS 3,330,282 A * 7/1967 Visser .................... A61J 1/2089
604/90
3,914,419 A * 10/1975 Haeger ................ A61K 9/0019
514/52

(Continued)

FOREIGN PATENT DOCUMENTS

EP  0 340 880 A2  11/1989
JP  H06209994 A   8/1994
(Continued)

OTHER PUBLICATIONS

International Search Report dated Apr. 12, 2017 in corresponding International Patent Application No. PCT/2017/052432.
(Continued)

*Primary Examiner* — Nathan R Price
*Assistant Examiner* — Justin L Zamory
(74) *Attorney, Agent, or Firm* — Medler Ferro Woodhouse & Mills PLLC

(57) ABSTRACT

A multi chamber syringe unit includes a body, a separating element and a bypass arrangement. The body has a distal end side, a proximal end side opposite to the distal end side, an interior limited by a side wall between the distal end side and the proximal end side and a longitudinal axis centrally extending from the distal end side to the proximal end side through the body. The separating element is arranged in the interior of the body forming a distal chamber between the distal end side and the separating element and a proximal chamber between the proximal end side and the separating element. The bypass arrangement is a section of the body in (Continued)

which the interior has a constant noncircular cross section orthogonal to the longitudinal axis. The multi camber syringe unit allows for being efficiently prepared and for efficiently providing or administering high quality of pre-filled products.

15 Claims, 3 Drawing Sheets

(51) Int. Cl.
    *A61M 5/31*     (2006.01)
    *A61J 1/20*     (2006.01)
    *A61M 5/28*     (2006.01)

(56) References Cited

U.S. PATENT DOCUMENTS

| | | | |
|---|---|---|---|
| 4,439,184 A * | 3/1984 | Wheeler | A61M 5/3129 604/191 |
| 4,469,482 A * | 9/1984 | Lissenburg | A61M 5/28 604/187 |
| 2016/0213447 A1* | 7/2016 | Yahav | B01F 13/0023 |

FOREIGN PATENT DOCUMENTS

| | | |
|---|---|---|
| JP | H08010325 A | 1/1996 |
| JP | H10052491 A | 2/1998 |
| JP | 2007-000719 A | 1/2007 |
| WO | 2006/058435 A2 | 6/2006 |
| WO | 2007/134066 A2 | 11/2007 |
| WO | 2015036992 A | 3/2015 |

OTHER PUBLICATIONS

Written Opinion dated Apr. 12, 2017 in corresponding International Patent Application No. PCT/2017/052432.
Japanese Office Action filed Jan. 5, 2021 for corresponding Japanese Patent Application No. 2018-540817.
Office Action dated Aug. 10, 2021 in Japanese Patent Appln No. 2018-540817 (with English language translation.).

* cited by examiner

MULTI CHAMBER SYRINGE UNIT

TECHNICAL FIELD

The present invention relates to a multi chamber syringe unit according to the preamble of independent claim 1. Such multi chamber syringe units can comprise a body with a bypass arrangement and a separating element. The body can have a distal end side, a proximal end side opposite to the distal end side, an interior limited by a side wall between the distal end side and the proximal end side and a longitudinal axis centrally extending from the distal end side to the proximal end side through the body. The separating element can be arranged in the interior of the body wherein it forms a distal chamber in the interior of the body between the distal end side and the separating element and a proximal chamber in the interior of the body between the proximal end side and the separating element. Multi chamber syringe units of this kind can be used for providing and applying one or plural pharmaceutical substances or mixtures to a patient.

BACKGROUND ART

Many pharmaceutical products are applied to patients in liquid form wherein injecting the product often is necessary or desired when administration needs to be very quick, e.g. in case of an emergency, or if the bioavailability via the gastro intestinal tract or other routes of administration is not sufficiently given. Particularly for subcutaneous, intramuscular, intradermal, intravitreal or other injections, the pharmaceutical substances are often provided in pre-filled syringes wherein staked-in needle prefilled syringes but also other syringes and cartridges or injectors have been shown to be comparably convenient to handle and use. In pre-filled syringes the pharmaceutical substance is provided in the interior of the syringe in a liquid form ready for being applied. Like this, the user receives a ready-to-inject syringe without the requirement to fill the pharmaceutical solution into the syringe or sometimes even without the need to manually assemble the needle to the syringe body. The occurrence of injuries or inappropriate handling during application can thereby be substantially lowered.

For pharmaceutical substances being unstable in liquid form such as many biopharmaceutical substances it is also known to provide the pharmaceutical substance in a freeze-dried or lyophilized form in which it is essentially more stable and robust compared to its liquid form. For delivering and applying such pharmaceutical substances specific double chamber syringes are used wherein one chamber houses the lyophilized pharmaceutical substance and the other a suitable diluent. Before being injected the lyophilized pharmaceutical substance is then reconstituted or solved in a diluent or liquid. Such reconstitution of the pharmaceutical substance inside the double chamber syringe is performed by transferring the diluent into the chamber of the lyophilized pharmaceutical substance and mixing the two. In liquid form, the pharmaceutical substance is then injected and delivered to the patient.

Usually double chamber syringes comprise a longitudinal, cylindrical body with a distal end side, a proximal end side and an interior between the distal end side and the proximal end side. In the interior of the body a rubber plunger is arranged which separates the interior of the body in a distal chamber and a proximal chamber. In an initial position the rubber plunger seals the proximal and the distal chamber from each other.

In many known double chamber syringes a bulge is formed in the body for allowing the rubber plunger to be bypassed. The bulge is positioned and dimensioned such that when the rubber plunger is arranged besides it liquid can pass the rubber plunger and be transferred between the proximal and distal chambers. For example, U.S. Pat. No. 4,874,381 A describes a two chambered syringe having a cylindrical body and a middle plunger separating the body into a distal chamber and a proximal chamber. In a side wall of the body a ridge-like bypass is formed as bulge. The syringe further comprises an activation rod extending into the body. By forwarding the activation rod, the middle plunger is moved until it lies adjacent to the bypass. Then the liquid passes the middle plunger via the bypass into the distal chamber.

Even though known double chamber syringes having bulge like bypasses can allow for a convenient application they usually have significant drawbacks in preparation. For example, for efficiently preparing prefilled double chamber syringes they usually are automatically processed. And since the bulge-like bypass prevents that the body is symmetric, specific measures have to be taken in order that the syringe is not damaged during preparation or in order to allow an efficient processing of the syringe. Such specific measures can make the preparation process comparably difficult and inefficient. Or, for example, in many cases products filled into double chamber syringes are inspected before the prefilled syringes are delivered. In particular, when pharmaceutical substances such as lyophilized substances are involved such inspection can be crucial in order to assure an appropriate quality. Typically, such inspections involve an optoelectronical or visual inspection which can also efficiently be performed in an automated manner. However, bulge-like bypasses in bodies of syringes can essentially hinder such optical inspection which can make the quality control of the prefilled product more complicated or less appropriate.

Therefore, there is need for a multi chamber syringe unit allowing to be efficiently prepared and for efficiently providing a high quality of prefilled products in administration.

DISCLOSURE OF THE INVENTION

According to the invention this need is fulfilled by a multi chamber syringe unit as it is defined by the features of independent claim 1. Preferred embodiments are subject of the dependent claims.

In particular, in one embodiment, the invention is a multi chamber syringe unit comprising a body, a separating element and a bypass arrangement. The body has a distal end side, a proximal end side opposite to the distal end side, an interior limited by a side wall between the distal end side and the proximal end side and a longitudinal axis centrally extending from the distal end side to the proximal end side through the body. The separating element is arranged in the interior of the body wherein it forms a distal chamber in the interior of the body between the distal end side and the separating element and a proximal chamber in the interior of the body between the proximal end side and the separating element. The bypass arrangement is provided in the body, e.g. in a side wall of the body. Particularly, the bypass arrangement is a section of the body in which the interior has a constant noncircular cross section orthogonal to the longitudinal axis.

The separating element can be made of an elastic material such as rubber or an elastic plastic material such as butyl. It can particularly be a rubber plunger. It can have an essentially piston-like shape. Further, it can be dimensioned to fit into the interior of the body such that it tightly seals the proximal chamber from the distal chamber when being positioned outside the influence of the bypass arrangement.

The term "bypass arrangement" as used herein can relate to a structure or element of the body allowing a liquid to pass the separating element. In particular, it can relate to a structure or element allowing the liquid to pass the separating element when the separating element is positioned besides or adjacent to the bypass arrangement.

The term "cross section" in connection with the interior of the body relates to a cross section in a plane perpendicular or orthogonal to the longitudinal axis of the body. In the section of the body being the bypass arrangement, the interior cross section is constant as well as noncircular. Thereby, the cross section is constant by having the same or essentially the same form or shape throughout the whole bypass arrangement. In particular, in the section of the body being the bypass arrangement, the interior cross section does essentially not vary along the longitudinal axis but stays essentially the same.

The term "noncircular" can relate to any suitable form which is not a circle. For example a form can be suitably which has some rounded corners. The noncircular cross section of the bypass arrangement allows a liquid to pass the separating element when the latter is in or at the bypass arrangement. Typically, the separating element is elastic such that when being moved into or at the bypass arrangement it is deformed. Thereby, it can loose its tightness such that liquid may pass by. In particular, the liquid can peripherally pass the separating element where openings or channels are formed due to the noncircular interior.

In a possible application of the multi chamber syringe unit, the proximal chamber is prefilled with a liquid and the distal chamber with another liquid or powder, e.g. a lyophilized pharmaceutical product to be solved. In an initial position, the separating element seals the proximal chamber from the distal chamber. During administration, the separating element is forwarded into or at the bypass arrangement, for example by pushing an activation rod into the proximal chamber. In the bypass arrangement the separating element is no longer seal such that the liquid can pass besides the separating element from the proximal chamber into the distal chamber. Thereby, according to the invention, the bypass being a noncircular section of the interior of the body allows for the liquid passing the separating element at plural locations. This can improve the mixing of the liquid from the proximal chamber with the liquid or powder of the distal chamber.

By providing the bypass arrangement as a section of the body in which the interior has a constant noncircular cross section, the multi chamber syringe unit allows for being shaped such that it can be efficiently handled regardless of its rotational orientation. In particular, it allows the body for being uniformly shaped at its outer surface such that it can be efficiently and easily processed particularly in an automated preparation process or facility. No alignment as it is known with syringes of the prior art is necessary. At the meantime the implementation of the bypass arrangement according to the invention allows for a comparably reliable and efficient optoelectronic and/or visual inspection of the interior of the section of the body where the bypass arrangement is located. In particular, this is made possible since comparably few disturbance of the optical path through the body can be involved with the bypass arrangement according to the invention. Visual inspections, which can be beneficial in certain situations, may include for example a visual control of liquid drug product before lyophilisation, visual control of lyophilized cake and/or visual control of liquid/liquid applications.

Furthermore, the side wall of the body can be comparably uniform and strong. More particularly, in conventional bulge forming the side wall, e.g. made of glass, at the bypass is weakened and therefore more prone to glass breakage. This can be efficiently prevented with the bypass as implemented according to the invention.

Thus, the multi camber syringe unit allows for being efficiently manufactured and prepared and for efficiently providing high quality of prefilled products in administration.

The multi chamber syringe unit can be a multi chamber cartridge such as a double chamber cartridge or a multi chamber syringe such as a double chamber syringe. For many advantageous applications it can be a staked-in needle pre-filled double chamber syringe. Thereby, the proximal chamber can be prefilled with a liquid which can serve as a diluent for a lyophilized substance such as a lyophilized pharmaceutical product.

Preferably, a first pharmaceutical liquid is arranged in the distal chamber of the body and a second pharmaceutical liquid in the proximal chamber of the body. Thereby, in one embodiment, the multi chamber syringe unit can be adapted for mixing the first pharmaceutical liquid with the second pharmaceutical liquid before injection. In particular, such embodiments allow injecting the two pharmaceutical liquids concomitantly.

For allowing such concomitant injection, the bypass arrangement can be located and shaped such that when the multi chamber syringe unit is activated, typically by pushing an activation rod into the proximal chamber, the second pharmaceutical liquid is transferred from the proximal chamber into the distal chamber. For example, pushing the activation rod may cause an increase of pressure inside the proximal chamber such that the separating element is moved towards the distal end side of the body. When it is located in or at the bypass arrangement, the second pharmaceutical liquid passes into the distal chamber. There it is mixed with the first pharmaceutical liquid. By further advancing the activation rod, the mixed first and second pharmaceutical liquids are pushed out of the body typically into a needle connected to the end side.

Alternatively, the multi chamber syringe unit can be arranged for sequentially providing the first and second pharmaceutical liquids. For this purpose, the multi chamber syringe unit can be adapted for, upon activation, initially providing the first pharmaceutical liquid out of the distal opening of the body and afterwards providing the second pharmaceutical liquid out of the distal opening of the body.

For allowing such sequential injection, the bypass arrangement preferably is located adjacent to the distal end side of the body. In this connection the term "adjacent" can be referred to as close to the distal end side as possible or feasible. The closer the bypass arrangement is located at the distal end side the less first pharmaceutical liquid is left in the interior of the body when the second pharmaceutical liquid passes via the bypass arrangement. Thereby, the body and the separating element preferably are arranged such that the distal chamber is essentially emptied when the separating element is moved to or located at the bypass arrangement.

In use of embodiments allowing for a sequential provision of a first and second pharmaceutical liquid, an activation rod may be pushed into the interior of the body which causes an increase of the pressure inside the proximal chamber. This causes the separating element to be moved towards the distal end side. Thereby, the pharmaceutical liquid of the distal chamber can be forced out of an opening or orifice provided in the distal end side of the body. When the separating element is located at the bypass arrangement, the distal chamber can be essentially empty. In this connection the term "essentially empty" can still allow some residues of the pharmaceutical liquid of the distal chamber. In particular, the space between the separating element and the distal end side may still contain some few of this pharmaceutical liquid left when the separating element is at the bypass arrangement. By further advancing the activation rod the liquid of the proximal chamber passes the separating element and is provided out of the distal opening of the body.

Thus, as the need may be, the multi chamber syringe unit allows for conveniently and safely providing a first and a second pharmaceutical liquid out of the body. In particular, the first and the second pharmaceutical liquid can be injected in a predefined and preferred manner, i.e. sequentially or concomitantly. Like this, the multi chamber syringe unit allows for adequately administering plural pharmaceutical liquids by injection.

Preferably, in an initial position, the bypass arrangement is located in the side wall of the body at the distal chamber. Such an arrangement of the bypass arrangement allows for efficiently applying the multi chamber syringe unit sequentially or concomitantly as described above. Also, it allows for efficiently manufacturing of the multi chamber syringe unit.

Preferably, aside from the bypass arrangement, the interior of the body has a circular cross section orthogonal to the longitudinal axis. Such a rotational symmetric shape of the body's interior allows efficiently providing the multi chamber syringe unit. Particularly, the separation element can be conventionally shaped, e.g. in the form of a plunger, post or piston.

Preferably, the outer surface of the body is constantly cylindrically shaped. The bypass arrangement can be embodied in the side wall of the body. Such outer surface allows for easily processing the double chamber syringe unit. In particular, within a preparation process, e.g. including prefilling the chambers and inspecting the prefilled substances, a cylindrical outer surface allows for efficiently handling the syringe unit. This can be an essential advantage in an automated preparation process or facility since it is not required to consider the rotational orientation of the double chamber syringe unit.

In one preferred embodiment, the interior in the section of the body being the bypass arrangement has an essentially oval-shaped cross section orthogonal to the longitudinal axis. Such an oval shape of the bypass arrangement allows for efficiently deforming the separation element and for unsealing the proximal and the distal chambers. Furthermore, such a bypass arrangement can comparably simply be built when manufacturing the body particularly when made of glass.

In another preferred embodiment, the interior in the section of the body being the bypass arrangement has an essentially polygonal-shaped cross section orthogonal to the longitudinal axis. Also such a shape of the bypass arrangement can be comparably easily manufactured and allows for efficiently deforming the separation element and for unsealing the proximal and the distal chambers.

Generally, for allowing the liquid to bypass the separation element as uniformly as possible in order to enable an even mixing once the liquid has bypassed the separation element, it is desirable to provide a polygonal-shaped cross section with as many corners as possible which also allows for efficiently deforming the separation element. However, contrary to such uniform bypassing providing a comparably high number of corners can decrease the quality of optical inspection within the bypass arrangement since comparably many disturbances of the optical paths may occur. Considering these two conflictive effects it has been found that the essentially polygonal-shaped cross section preferably essentially has the form of a triangle, a square, a pentagon or a hexagon. Such a polygonal shape allows for a sufficiently uniform bypassing of the liquid and an efficient optical inspection. Thereby, the essentially polygonal-shaped cross section preferably has rounded corners. Such rounded corners allow the body to be efficiently manufactured and to minimize disturbance of the optical inspection.

Preferably, the multi chamber syringe unit comprises an actuation rod extending into the proximal chamber. Such an actuation rod allows for efficiently forcing the separating element into or adjacent to the bypass arrangement and for supplying the content out of the body. For example, by pushing the actuation rod into the interior of the proximal chamber the pressure in this chamber can be raised. The raised pressure can then move the separating element along the axis until it lies in or adjacent to the bypass arrangement. Thereby, the separating element preferably is movable by forwarding the actuation rod into the proximal chamber of the body.

Preferably, the body is made of a transparent material such as glass. Such a transparent material allows for an efficient optical inspection of the content of the body. Using glass as material of the body further allows for efficiently providing the content of the body in a sterile and robust manner.

Preferably, an orifice is arranged in the distal end side of the body for providing a liquid out of the body. The orifice can comprise a needle or a connector allowing a needle to be mounted to the body. Such an orifice allows for supplying the content of the body. In particular, the liquid can be provided out of the interior of the body via the orifice.

In addition to the separation element, the multi chamber syringe unit may comprise a closing element arranged in the interior of the body closing the proximal chamber. The closing element can be a plunger such as an end plunger. Such a closing element allows for efficiently sealing the proximal chamber and preventing contamination.

BRIEF DESCRIPTION OF THE DRAWINGS

The multi chamber syringe unit according to the invention is described in more detail herein below by way of exemplary embodiments and with reference to the attached drawings in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
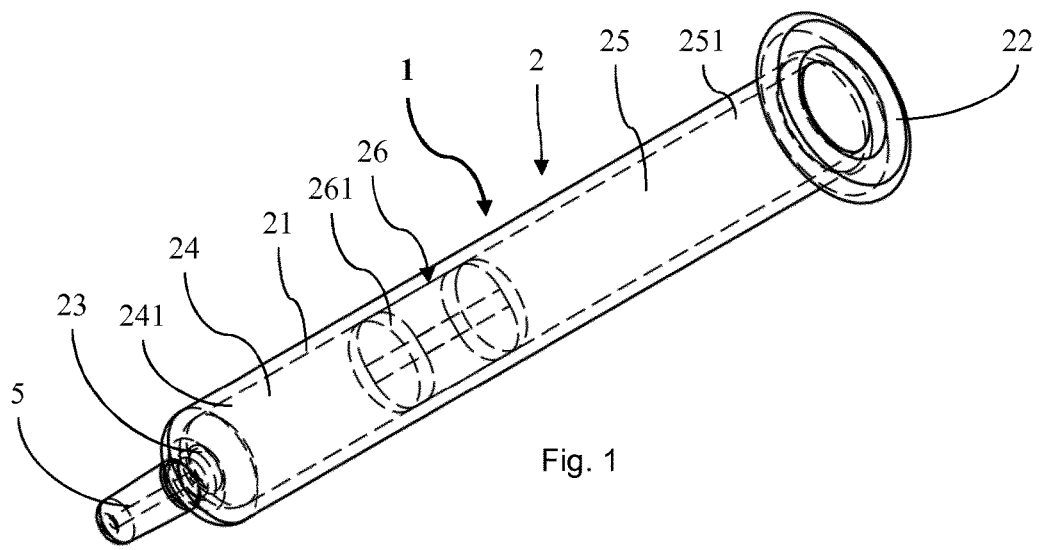
FIG. 1 shows a perspective view of a body of a first embodiment of a double chamber syringe as a first embodiment of a multi chamber syringe unit according to the invention.

FIG. 1 shows a longitudinal hollow glass body 2 of a pre-filled double chamber syringe 1 as a first embodiment of a multi chamber syringe unit according to the invention. The body 2 has a tubular side wall 21 surrounding an interior of the body 2. At its one end in a longitudinal direction, in FIG. 1 this is the left end, the body 2 has a distal end side 23 which is equipped with a distal opening passing over in a needle connector 5. At its other opposite end in the longitudinal direction, in FIG. 1 this is the right end, the body 2 has a proximal end side 22 having a proximal opening.

The interior of the body 2 has a distal chamber 24 near the distal end side 23 and a proximal chamber 25 near the proximal end side 22. Further, a section of the body 2 is formed as bypass arrangement 26. This is, in contrast to the rest for the body 2 where a distal cross section 241 of its interior in the distal chamber 24 and a proximal cross section 251 of its interior in the proximal chamber 25 are circular, in the section of the body 2 forming the bypass arrangement 26 a bypass cross section 261 of the interior is noncircular. More specifically, the interior of the complete section of the body 2 forming the bypass arrangement 26 constantly and uniformly has the noncircular bypass cross section 261.

Figure 2:
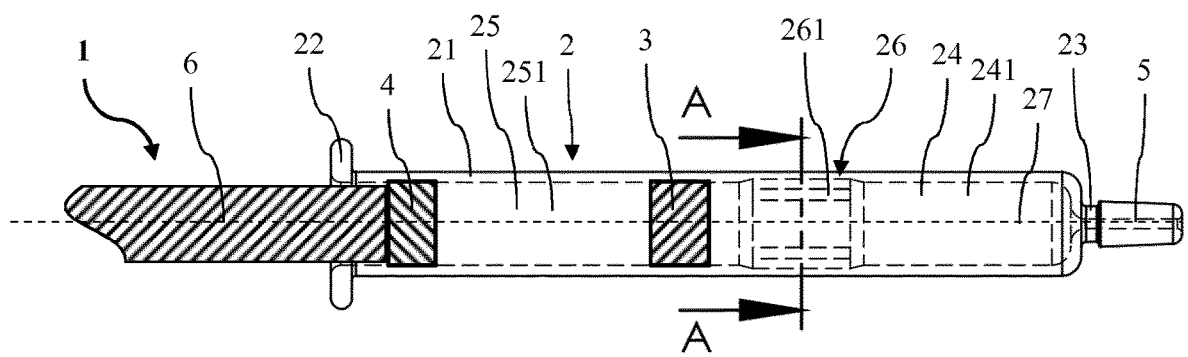
FIG. 2 shows a side view of the double chamber syringe of FIG. 1.

As can be seen in FIG. 2, in the interior of the body 2 a middle plunger 3 as a separation element and an end plunger 4 as a closing element are arranged. Between the middle plunger 3 and the distal end side 23 the distal chamber 24 is formed in the interior of the body 2. Similarly, between the middle plunger 3 and the end plunger 4 the proximal chamber 25 is formed in the interior of the body 2. In the distal chamber 24 of the body 2 a first pharmaceutical liquid and in the proximal chamber 25 of the body 2 a second pharmaceutical liquid are arranged. In the initial position shown in FIG. 2, the middle plunger 3 is located offside the bypass arrangement 26. It is located in a section of the interior of the body 2 having the circular proximal cross section 251. The middle plunger 3 is piston like shaped and made of an elastic material. In the position of FIG. 2, it is slightly compressed and seals the proximal chamber 24 from the distal chamber 25 such that the first and second pharmaceutical liquids are safely separated from each other.

The syringe 1 has a longitudinal axis 27 extending through the body 2 from its distal end side 23 to its proximal end side 22. It is further equipped with an activating rod 6 which extends through the proximal opening at the proximal end side 22 along the longitudinal axis 27 into the interior of the body 2. The proximal end side 22 of the body 2 has a finger flange radially extending above the rest of the body 2. In the initial position shown in FIG. 2, the bypass arrangement 26 is located in the distal chamber 24.

Figure 3:
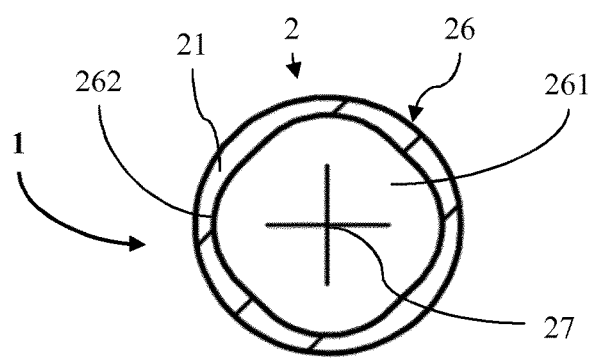
FIG. 3 shows a cross sectional view along the line A-A of FIG. 2.

In FIG. 3 the bypass arrangement 26 of the body 2 is shown in more detail. In particular, the bypass cross section 261 of the interior of the section of the body 2 forming the bypass arrangement 26 is visible. The bypass cross section 261 lies in a plane orthogonal to the axis 27. It essentially has the shape of a square wherein the four corners 262 are rounded. Such rounded corners 262 are beneficial in manufactory and use of the syringe 1. The outer periphery of the body 2 is circular in its cross section. Thus, the side wall 21 is embodied variably thick in order to implement the noncircular bypass cross section 261.

In use, the syringe 1 is operated by pushing the activating rod 6 into the interior of the body 2, i.e. into the proximal chamber 25. Thereby, a force is applied to a finger rest of the rod 6 which, e.g. can be done by a thumb of a hand. The pressure inside the proximal chamber 25 is increased by the force acting on the rod 6 and the middle plunger 3 is moved into the direction of the distal end side 23 of the body 2 until it lies adjacent to or at the bypass arrangement 26. In this position, the middle plunger 3 is deformed by the noncircular bypass cross section 261 and plural channels are formed besides the middle plunger 3 at the corners 262 of the bypass cross section 261.

By further advancing the activating rod 6, the second pharmaceutical liquid bypasses the middle plunger 3 and is transferred from the proximal chamber 25 into the distal chamber 24 wherein the middle plunger 3 is not moving. There, the first pharmaceutical liquid is mixed with the second pharmaceutical liquid. By still further advancing the activating rod 6, the middle plunger 3 moves further into the direction of the distal end side 23 and pushes the mixture of first and second pharmaceutical liquids through the needle connector 5 out of the syringe 1.

As is commonly known, in use in a therapeutic application, a needle mounted to the needle connector 5 penetrates a target tissue, e.g. subcutaneously, and the syringe is activated, e.g. by the patient, as described above. Thereby, the first and second pharmaceutical liquids are to a major extent injected concomitantly.

Figure 4:
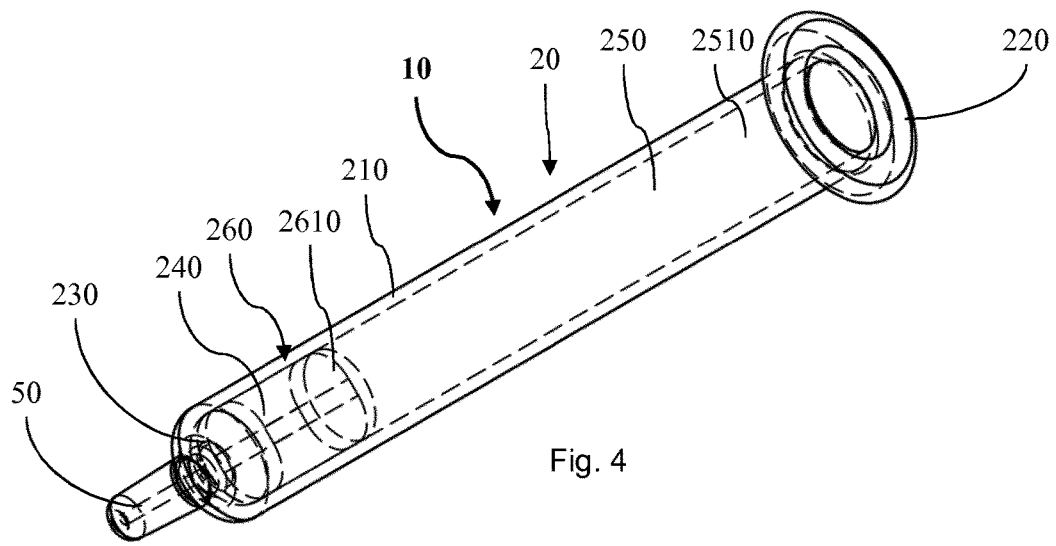
FIG. 4 shows a perspective view of a body of a second embodiment of a double chamber syringe as a second embodiment of a multi chamber syringe unit according to the invention.
Figure 5:
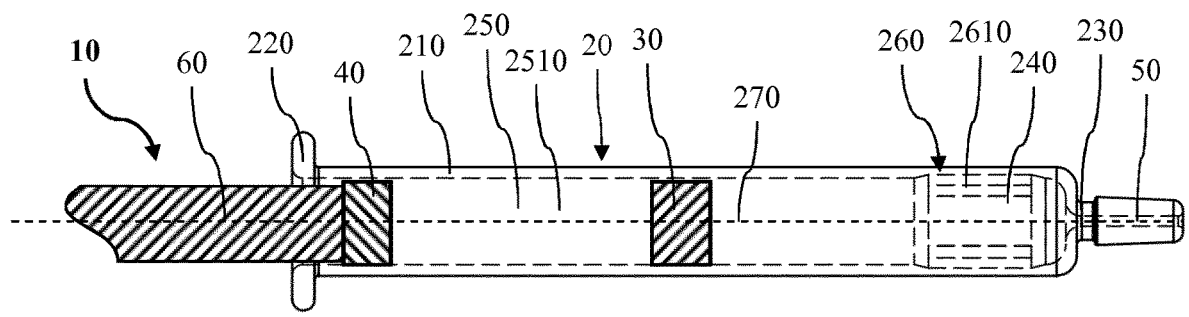
FIG. 5 shows a side view of the double chamber syringe of FIG. 4.

In FIG. 4 and FIG. 5 a pre-filled double chamber syringe 10 is shown as a second embodiment of a multi chamber syringe unit according to the invention. The syringe 10 has a longitudinal hollow glass body 20 with a longitudinal axis 270 and a tubular side wall 210 surrounding an interior of the body 20. At its one end in a longitudinal direction, the body 20 has a distal end side 230 which is equipped with a distal opening passing over in a needle connector 50. At its other opposite end in the longitudinal direction, the body 20 has a proximal end side 220 having a proximal opening and a finger flange portion.

Adjacent to the distal end side 230 the body 210 has a bypass arrangement 260. In the interior of the body 20 a middle plunger 30 as a separation element and an end plunger 40 as a closing element are arranged. Between the middle plunger 30 and the distal end side 230 a distal chamber 240 is formed in the interior of the body 20. Similarly, between the middle plunger 30 and the end plunger 40 a proximal chamber 250 is formed in the interior of the body 20. In the distal chamber 240 of the body 20 a first pharmaceutical liquid is arranged. In the proximal chamber 250 of the body 20 a second pharmaceutical liquid is arranged.

Figure 6:
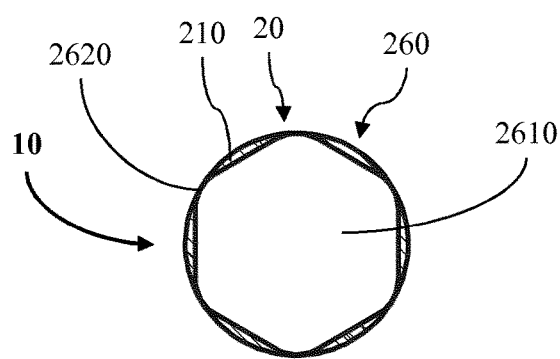
FIG. 6 shows a cross sectional view of a bypass arrangement of the double chamber syringe of FIG. 5.

In the initial position shown in FIG. 5, the middle plunger 30 is located offside the bypass arrangement 260. It is located in a section of the interior of the body 20 having the circular proximal cross section 2510. The middle plunger 30 is piston like shaped and made of an elastic material. In the position of FIG. 6, it is slightly compressed and seals the proximal chamber 240 from the distal chamber 250 such that the first and second pharmaceutical liquids are safely separated from each other.

The syringe 10 is further equipped with an activating rod 60 which extends through the proximal opening at the proximal end 220 into the interior of the body 20. The activating rod 60 has a finger rest and is connected to the end plunger 40.

In FIG. 6 the bypass arrangement 260 of the body 20 is shown in more detail. In particular, the bypass cross section 2610 of the interior of the section of the body 20 forming the bypass arrangement 260 is visible. The bypass cross section 2610 lies in a plane orthogonal to the axis 270. It essentially has the shape of a hexagon wherein the six corners 2620 are rounded. Such rounded corners 2620 are beneficial in manufactory and use of the syringe 10. The outer periphery of the body 20 is circular in its cross section. Thus, the side wall 210 is embodied variably thick in order to implement the noncircular bypass cross section 2610.

The syringe 10 is operated by pushing the activating rod 60 into the interior of the body 20. Thereby, the operation is initiated by applying a force to the finger rest of the rod 60 which, e.g. can be done by a thumb of a hand. A pressure inside the proximal chamber 250 is increased and the middle plunger 30 is moved into the direction of the distal end side 230 of the body 20. During this movement of the middle plunger 30 the first pharmaceutical liquid is provided through the needle connector 50 out of the distal chamber 240. Thereby, the middle plunger 30 is moved as far such that it lies adjacent to or at the bypass arrangement 260.

In this position, the middle plunger 30 is deformed by the noncircular bypass cross section 2610 and plural channels are formed besides the middle plunger 30 at the corners 2620 of the bypass cross section 2610. The first pharmaceutical liquid originally arranged in the distal chamber 240 of the body 20 is, to a large extent, already pushed out of the syringe 10 via the needle connector 50. The second pharmaceutical substance 80 starts to pass the middle plunger 30 via the bypass channels. By further advancing the activating rod 60, the second pharmaceutical liquid 80 more and more bypasses the middle plunger 30 and is transferred from the proximal chamber 250 via the distal chamber 240 through the needle connector 50 out of the interior of the body 20.

In use, in a therapeutic application a needle mounted to the needle connector 50 penetrates a target tissue, e.g. subcutaneously, and the syringe 10 is activated, e.g. by the patient, as described above. Thereby, the first and second pharmaceutical liquid are injected sequentially. In particular, since the bypass arrangement 260 is located close or adjacent to the distal end side 230 of the body 20 the distal chamber 240 is essentially emptied before the second pharmaceutical liquid bypasses the middle plunger 30. Only in a transition situation there is, for a comparably short time, a mixture of the first and second pharmaceutical liquids provided. However, it can efficiently be achieved that the first and second pharmaceutical liquids are administered one after the other.

Figure 7:
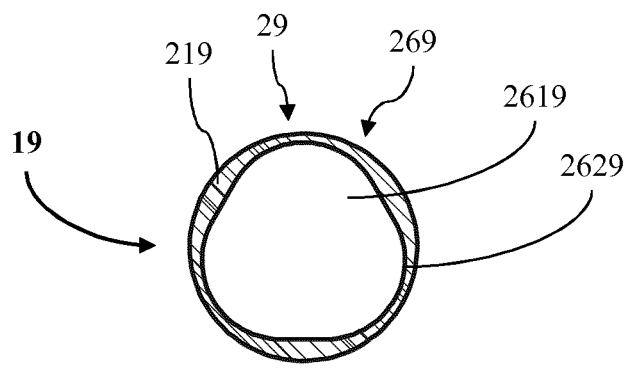
FIG. 7 shows a cross sectional view of a bypass arrangement of a third embodiment of a multi chamber syringe unit according to the invention.

FIG. 7 shows a bypass arrangement 269 of a body 29 of a double chamber syringe 19 as a third embodiment of a multi chamber syringe unit. The bypass arrangement 269 has an interior with a cross section 2619 which is triangle-like shaped. More particular, the triangle of the cross section 2619 of the bypass arrangement has rounded corners 2629. These rounded corners 2629 allow for being efficiently provided in a side wall 219 of the body 29 of the syringe 19.

Figure 8:
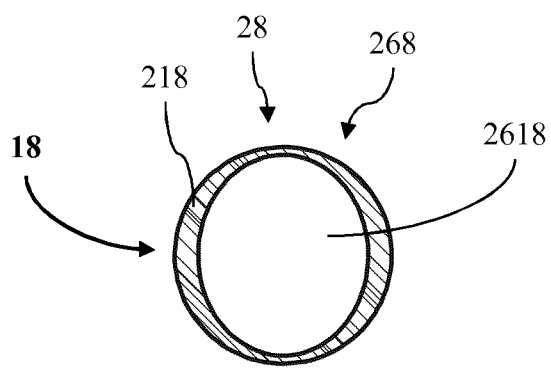
FIG. 8 shows a cross sectional view of a bypass arrangement of a fourth embodiment of a multi chamber syringe unit according to the invention.

In FIG. 8 a bypass arrangement 268 of a body 28 of a double chamber syringe 18 as a fourth embodiment of a multi chamber syringe unit is shown. The bypass arrangement 268 has an interior with a cross section 2618 which is ellipsoid. Such an ellipsoid shape can be embodied in a side wall 218 of the body 28 in a comparable simple manner.

This description and the accompanying drawings that illustrate aspects and embodiments of the present invention should not be taken as limiting the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A multi chamber syringe unit comprising:
    a body with a distal end side, a proximal end side opposite to the distal end side, an interior limited by a side wall between the distal end side and the proximal end side and a longitudinal axis centrally extending from the distal end side to the proximal end side through the body;
    a separating element arranged in the interior of the body, wherein the separating element forms a distal chamber in the interior of the body between the distal end side and the separating element and a proximal chamber in the interior of the body between the proximal end side and the separating element; and
    a bypass arrangement provided in the body, wherein the bypass arrangement is a section of the body in which the interior has a constant essentially polygonal-shaped cross section orthogonal to the longitudinal axis and wherein the essentially polygonal-shaped cross section has rounded corners and does not have any vertices to form a continuous inner surface without edges along a length of the bypass arrangement and thereby minimize disturbance of an optical inspection of the bypass arrangement,
    wherein the essentially polygonal-shaped cross section of the interior of the bypass arrangement is configured to deform the separating element and form a plurality of channels beside the separating element.

2. The multi chamber syringe unit according to claim 1, wherein, aside from the bypass arrangement, the interior of the body has a circular cross section orthogonal to the longitudinal axis.

3. The multi chamber syringe unit according to claim 1, wherein the essentially polygonal-shaped cross section essentially has the form of a triangle, a square, a pentagon or a hexagon.

4. The multi chamber syringe unit according to claim 1, wherein an outer surface of the body is constantly cylindrically shaped.

5. The multi chamber syringe unit according to claim 1, wherein a first pharmaceutical liquid is arranged in the distal chamber of the body; and a second pharmaceutical liquid is arranged in the proximal chamber of the body.

6. The multi chamber syringe unit according to claim 1, wherein, in an initial position, the bypass arrangement is located in the side wall of the body at the distal chamber.

7. The multi chamber syringe unit according to claim 1, wherein the bypass arrangement is located adjacent to the distal end side of the body.

8. The multi chamber syringe unit according to claim 1, comprising an actuation rod extending into the proximal chamber.

9. The multi chamber syringe unit according to claim 8, wherein the separating element is movable by forward movement of the actuation rod into the proximal chamber of the body.

10. The multi chamber syringe unit according to claim 7, wherein the body and the separating element are arranged such that the distal chamber is essentially emptied when the separating element is moved to the bypass arrangement.

11. The multi chamber syringe unit according to claim 1, wherein the body is made of a transparent material such as glass.

12. The multi chamber syringe unit according to claim 1, wherein an orifice is arranged in the distal end side of the body for providing a liquid out of the body.

13. The multi chamber syringe unit according to claim 10, comprising an actuation rod extending into the proximal chamber.

14. The multi chamber syringe unit according to claim 13, wherein the separating element is movable by forward movement of the actuation rod into the proximal chamber of the body.

15. The multi chamber syringe unit according to claim 1, wherein the plurality of channels are formed beside the separating element at the rounded corners of the essentially polygonal-shaped cross section.

\* \* \* \* \*